(12) United States Patent
Takahashi et al.

(10) Patent No.: US 12,020,919 B2
(45) Date of Patent: Jun. 25, 2024

(54) METHOD FOR ANALYZING ISOASPARTIC ACID AND MASS SPECTROMETER

(71) Applicants: SHIMADZU CORPORATION, Kyoto (JP); NATIONAL INSTITUTE OF ADVANCED INDUSTRIAL SCIENCE AND TECHNOLOGY, Tokyo (JP)

(72) Inventors: Hidenori Takahashi, Kyoto (JP); Daiki Asakawa, Tsukuba (JP)

(73) Assignees: SHIMADZU CORPORATION, Kyoto (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 310 days.

(21) Appl. No.: 17/597,350

(22) PCT Filed: Jul. 14, 2020

(86) PCT No.: PCT/JP2020/027388
§ 371 (c)(1),
(2) Date: Jan. 4, 2022

(87) PCT Pub. No.: WO2021/010401
PCT Pub. Date: Jan. 21, 2021

(65) Prior Publication Data
US 2022/0254621 A1    Aug. 11, 2022

(30) Foreign Application Priority Data
Jul. 17, 2019  (JP) ................................ 2019-132268

(51) Int. Cl.
*H01J 49/14*   (2006.01)
*G01N 27/64*   (2006.01)
(Continued)

(52) U.S. Cl.
CPC .............. *H01J 49/14* (2013.01); *G01N 27/64* (2013.01); *H01J 49/0031* (2013.01); *H01J 49/40* (2013.01)

(58) Field of Classification Search
CPC ........ H01J 49/14; H01J 49/0031; H01J 49/40; H01J 49/0045; G01N 27/64; G01N 27/62;
(Continued)

(56) References Cited

U.S. PATENT DOCUMENTS

2016/0266141 A1* 9/2016 Li ...................... G01N 33/6848
2016/0372311 A1  12/2016 Takahashi et al.
(Continued)

FOREIGN PATENT DOCUMENTS

EP    3460826 A1    3/2019
JP    2018-044826 A    3/2018
(Continued)

OTHER PUBLICATIONS

Second Office Action dated Jun. 6, 2023 issued for the corresponding Japanese Patent Application No. 2021-533081.
(Continued)

*Primary Examiner* — Kiet T Nguyen
(74) *Attorney, Agent, or Firm* — Sughrue Mion, PLLC

(57) ABSTRACT

In a method for analyzing isoaspartic acid by dissociating precursor ions derived from a sample component and generating and analyzing product ions, the method includes: generating product ions by irradiating the precursor ions with hydrogen radicals or radicals having oxidizing ability to dissociate the precursor ions; separating and detecting the product ions according to a mass-to-charge ratio; and specifying product ions derived from isoaspartic acid based on a mass-to-charge ratio of the product ions.

8 Claims, 4 Drawing Sheets

(51) Int. Cl.
  *H01J 49/00* (2006.01)
  *H01J 49/40* (2006.01)
(58) Field of Classification Search
  CPC ........... G01N 33/6812; G01N 33/6848; G01N 2800/166
  USPC .................................................. 250/281, 282
  See application file for complete search history.

(56) References Cited

U.S. PATENT DOCUMENTS

| | | | |
|---|---|---|---|
| 2018/0356426 A1 | 12/2018 | Ayrton et al. | |
| 2019/0073452 A1* | 3/2019 | Li | G01N 33/6851 |
| 2020/0111654 A1 | 4/2020 | Takahashi et al. | |
| 2023/0366889 A1* | 11/2023 | Hui | G01N 33/6848 |

FOREIGN PATENT DOCUMENTS

| | | |
|---|---|---|
| WO | 2015/133259 A1 | 9/2015 |
| WO | 2018/186286 A1 | 10/2018 |

OTHER PUBLICATIONS

Takumi Takata, "Study on the mechanism of cataract onset caused by spontaneous chemical modification of amino acids in lens constituent proteins", Journal of the Japanese Society for Cataract, 2018, 12 pgs., vol. 30.

Lisanne J. M. Kempkes et al., "Deamidation Reactions of Asparagine- and Glutamine-Containing Dipeptides Investigated by Ion Spectroscopy", J. Am. Soc. Mass Spectrom., 2016, 15 pgs.

Doshisha University et al., "Development of a Compact Atom Beam Source by Capacitively Coupled Plasma at 2.45GHz", 77th Japan Society of Applied Physics Autumn Academic Lecture Proceedings, 2016, 2 pgs.

Yuji Shimabukuro et al., "Tandem Mass Spectrometry of Peptide Ions by Microwave Excited Hydrogen and Water Plasmas", Analytical Chemistry, May 24, 2018, pp. 7239-7245, vol. 90.

Koichi et al., "Simultaneous Determination of Post-Translational Racemization and Isomerization of N-Terminal Amyloid-β in Alzheimer's Brain Tissues by Covalent Chiral Derivatized Ultraperformance Liquid Chromatography Tandem Mass Spectrometry", Analytical Chemistry, Nov. 27, 2013, pp. 797-804, vol. 86.

Shunhai Wang et al., "An $^{18}$O-Labeling Assisted LC/MS Method for Assignment of Aspartyl/Isoaspartyl Products from Asn Deamidation and Asp Isomerization in Proteins", Analytical Chemistry, May 28, 2013, pp. 6446-6452, vol. 85, No. 13.

Nick Degraan-Weber et al., "Distinguishing Aspartic and Isoaspartic Acids in Peptides by Several Mass Spectrometric Fragmentation Methods", J. Am. Soc Mass Spectrom., 2016, pp. 2041-2053, vol. 27.

Daiki Asakawa et al., "Difference of Electron Capture and Transfer Dissociation Mass Spectrometry on Ni2+-, Cu2+-, and Zn2+-Polyhistidine Complexes in the Absence of Remote Protons", J. Am. Soc. Mass Spectrom., 2016, pp. 1165-1175, vol. 27.

Written Opinion of the International Searching Authority for PCT/JP2020/027388 dated Sep. 24, 2020 (PCT/ISA/237).

International Search Report for PCT/JP2020/027388 dated Sep. 24, 2020 (PCT/ISA/210).

Hidenori Takahashi et al., "Hydrogen Attachment/Abstraction Dissociation (HAD) of Gas-Phase Peptide Ions for Tandem Mass Spectrometry", Analytical Chemistry, Mar. 22, 2016, vol. 88, No. 7, pp. 3810-3816 (7 pages total).

Hidenori Takahashi et al., "Structural Analysis of Phospholipid Using Hydrogen Abstraction Dissociation and Oxygen Attachment Dissociation in Tandem Mass Spectrometry", Analytical Chemistry, May 24, 2018, vol. 90, No. 12, pp. 7230-7238 (9 pages total).

Nadezda P. Sargaeva et al., "Deamidation and Related Problems in Structural Analysis of Peptides and Proteins", Boston University School of Medicine Dissertation, Jan. 1, 2012, Retrieved from the Internet: URL:https://www.bumc.bu.edu/ftms/files/2016/08/Sargaeva_Thesis_Final.pdf, (202 total pages).

Wai Yi Kelly Chan et al., "Electron Transfer Dissociation with Supplemental Activation to Differentiate Aspartic and Isoaspartic Residues in Doubly Charged Peptide Cations", Journal of the American Society for Mass Spectrometry, Jun. 1, 2010, vol. 21, No. 6, pp. 1012-1015 (4 pages total).

Wenqin Ni et al., "Analysis of Isoaspartic Acid by Selective Proteolysis with Asp-N and Electron Transfer Dissociation Mass Spectrometry", Anal. Chem., Sep. 1, 2010, vol. 82, No. 17, pp. 7485-7491 (7 pages total).

Extended European Search Report dated Aug. 1, 2022 in Application No. 20841023.3.

European Office Action dated Aug. 22, 2023 for Application No. 20841023.3.

Japanese Office Action dated Sep. 5, 2023 for Patent Application No. 2021-533081.

First Office Action dated Jan. 10, 2023 issued for the corresponding Japanese Patent Application No. 2021-533081.

Office Action issued Feb. 29, 2024 in Chinese Application No. 202080051664.4.

* cited by examiner

DISCRIMINATION BETWEEN ASPARTIC ACID AND ISOASPARTIC ACID

MASS OF c ION IS SAME
MASS OF FRAGMENT OF Cα-C CLEAVAGE IS DIFFERENT

FRAGMENTATION OF ISOASPARTIC ACID RESIDUE

GENERATION OF c'-57 AND z+57, UNIQUE FRAGMENT ION OF ISOASPARTIC ACID BY HAD IS EXPECTED

AS EXPECTED FROM QUANTUM CHEMICAL CALCULATION, [z+57] IS GENERATED WHEN ISOASPARTIC ACID RESIDUE EXISTS

CONFIRMED THAT FRAGMENT ON N-TERMINAL SIDE IS [c-57] ISOASPARTIC ACID RESIDUE CAN BE IDENTIFIED BY HAD-MS$^2$

METHOD FOR ANALYZING ISOASPARTIC ACID AND MASS SPECTROMETER

CROSS REFERENCE TO RELATED APPLICATIONS

This application is a National Stage of International Application No. PCT/JP2020/027388 filed Jul. 14, 2020, claiming priority based on Japanese Patent Application No. 2019-132268 filed Jul. 17, 2019.

TECHNICAL FIELD

The present invention relates to a method for analyzing isoaspartic acid, and a mass spectrometer for performing the analysis method.

BACKGROUND ART

It has been reported that aspartic acid, which is a kind of amino acid constituting a protein, is isomerized to isoaspartic acid over time, and becomes a factor causing cataract (for example, Non Patent Literature 1). Therefore, analyzing the isoaspartic acid contained in a peptide contained in a biological metabolite and estimating how much isoaspartic acid is accumulated in the body based on the result may be effective for grasping the risk of cataract occurrence and considering measures for prevention of cataract.

In order to identify a high polymer compound such as protein, a type of mass spectrometry is widely used in which ions derived from a high polymer compound (precursor ions) are dissociated one or more times to generate product ions (also referred to as fragment ions), and the product ions are separated according to mass-to-charge ratio and detected. As a representative method for dissociating ions in such mass spectrometry, a collision-induced dissociation (CID) method in which molecules of an inert gas such as nitrogen gas are made to collide with ions is known. However, in the CID method, there is no difference between a product ion generated by dissociation of a precursor ion derived from a peptide containing an isoaspartic acid residue and a product ion generated by dissociation of a precursor ion derived from a peptide containing an aspartic acid residue which is an isomer of the isoaspartic acid residue. Therefore, even when ions are dissociated by the CID method, isoaspartic acid and aspartic acid cannot be discriminated from each other.

Non Patent Literature 1 describes that when a negative ion is collided with a positive precursor ion derived from a peptide containing an isoaspartic acid residue to cause electron transfer dissociation (ETD), product ions that are characteristic of isoaspartic acid, such as c+57 ions and z−57 ions, are generated. The c+57 ion is an ion having a mass larger by 57 Da than the ion (c ion) on the N-terminal side generated by cleaving the N—Cα bond of the peptide main chain of aspartic acid. The z−57 ion is an ion having a mass smaller by 57 Da than the ion (z ion) on the C-terminal side generated by cleaving the N—Cα bond. Here, the product ion generated from the precursor ion derived from the peptide containing the isoaspartic acid residue is expressed based on the c ion and the z ion of the peptide containing the aspartic acid residue because the bond of the peptide main chain is different between the isoaspartic acid residue and the aspartic acid residue, so that the definition of the c ion and the z ion may be unclear.

CITATION LIST

Patent Literature

Patent Literature 1: WO 2015/133259 A

Non Patent Literature

Non Patent Literature 1: Takata Takumi, "The Spontaneous Amino-acid Modifications and Those Contributions for the Aged Lens Proteins", Journal of Japan Cataract Society, 30, pp. 7-12, 2018

Non Patent Literature 2: Kempkes, L, J., Martens, J., Grzetic, J., Berden, G., & Oomens, J., "Deamidation Reactions of Asparagine- and Glutamine-Containing Dipeptides Investigated by Ion Spectroscopy", Journal of the American Society for Mass Spectrometry, 27(11), pp. 1855-1869, 2016

Non Patent Literature 3: Shimabukuro, Kasuya, Wada, "Development of a Compact Atom Beam Source by Capacitively Coupled Plasma at 2.45 GHz". Proc. of the 77th JSAP Academic Lecture, September 2016, Japan Society of Applied Physics Non Patent Literature 4: Yuji Shimabukuro, Hidenori Takahashi, Shinichi Iwamoto, Koichi Tanaka, Motoi Wada, "Tandem Mass Spectrometry of Peptide Ions by Microwave Excited Hydrogen and Water Plasmas", Anal. Chem. 2018, 90(12) pp 7239-7245

SUMMARY OF INVENTION

Technical Problem

In the ETD method, since negative ions are collided with positive precursor ions to generate product ions, only divalent or more precursor ions can be dissociated. In addition, ions generated by a soft ionization method such as the matrix-assisted laser desorption/ionization (MALDI) method used for ionization of proteins and peptides are mostly monovalent ions. Therefore, in the combination of the MALDI method or the like and the ETD method, the dissociation efficiency of precursor ions is poor, and the above-described ions characterizing isoaspartic acid cannot be detected with sufficient intensity, and thus there is a problem that it is difficult to discriminate isoaspartic acid and aspartic acid.

An object of the present invention is to provide a technique capable of easily discriminating isoaspartic acid and aspartic acid contained in a sample.

Solution to Problem

One aspect of the present invention developed for solving the above-mentioned problems is a method for analyzing isoaspartic acid by dissociating precursor ions derived from a peptide component and generating and analyzing product ions, the method including:
  generating product ions by irradiating the precursor ions with hydrogen radicals or radicals having oxidizing ability to dissociate the precursor ions;
  separating and detecting the product ions according to a mass-to-charge ratio; and
  specifying product ions derived from isoaspartic acid based on a mass-to-charge ratio of the product ions.

Another aspect of the present invention developed for solving the above-mentioned problems is a mass spectrometer for analyzing isoaspartic acid by generating product ions from precursor ions derived from a sample component and analyzing the product ions, the mass spectrometer including:
- a reaction chamber into which the precursor ions are introduced;
- a radical generation unit configured to generate a hydrogen radical or aradical having oxidizing ability;
- a radical irradiation unit configured to irradiate an inside of the reaction chamber with radicals generated by the radical generation unit;
- a separation and detection unit configured to separate and detect product ions generated by dissociation of the precursor ions by reaction with the radicals according to a mass-to-charge ratio; and
- a product ion specifying unit configured to specify product ions derived from isoaspartic acid on a basis of a mass-to-charge ratio of the product ions.

Advantageous Effects of Invention

In a method for analyzing isoaspartic acid and a mass spectrometer according to the present invention, precursor ions derived from the sample component are irradiated with hydrogen radicals or radicals having oxidizing ability to generate product ions. The radical having oxidizing ability is, for example, an oxygen radical or a hydroxy radical. The ion dissociation method for irradiating precursor ions with these radicals is a hydrogen-attachment dissociation (HAD) method and an oxygen-attachment dissociation (OAD) method proposed by the present inventor in Patent Literature 1.

The present inventor has found that when the precursor ions derived from isoaspartic acid are dissociated by the HAD method, c+57 ions and z−57 ions which characterize isoaspartic acid (and are not generated from aspartic acid) are generated as in the ETD method. In addition, the present inventor has found that when precursor ions derived from isoaspartic acid are dissociated by the OAD method, a+16 ions and/or x ions are generated. The a+16 ion is an ion having a mass larger by 16 Da than that of the ion (a ion) on the N-terminal side which is generated by cleaving the Cα-C bond of the peptide main chain of aspartic acid. Since both the a+16 ion and the x ion generated from the isoaspartic acid residue have different masses from that derived from the aspartic acid residue, it is possible to discriminate these residues according to the present invention.

That is, the present inventor has found that isoaspartic acid can be discriminated from aspartic acid and analyzed by separating and detecting product ions generated by dissociating precursor ions derived from a sample component according to a mass-to-charge ratio and specifying c+57 ions, z−57 ions, a+16 ions, or x ions from the product ions. The HAD method and the OAD method are methods of dissociating precursor ions by radical addition, and can be used regardless of the polarity or valence of ions to be dissociated. Therefore, precursor ions derived from a sample component can be efficiently dissociated, and the isoaspartic acid and the aspartic acid, which is an isomer of the isoaspartic acid, can be easily discriminated.

DESCRIPTION OF EMBODIMENTS

One embodiment of a mass spectrometer according to the present invention will be described below with reference to the drawings. The mass spectrometer of the embodiment is an ion trap-time-of-flight (IT-TOF) mass spectrometer.

Figure 1:
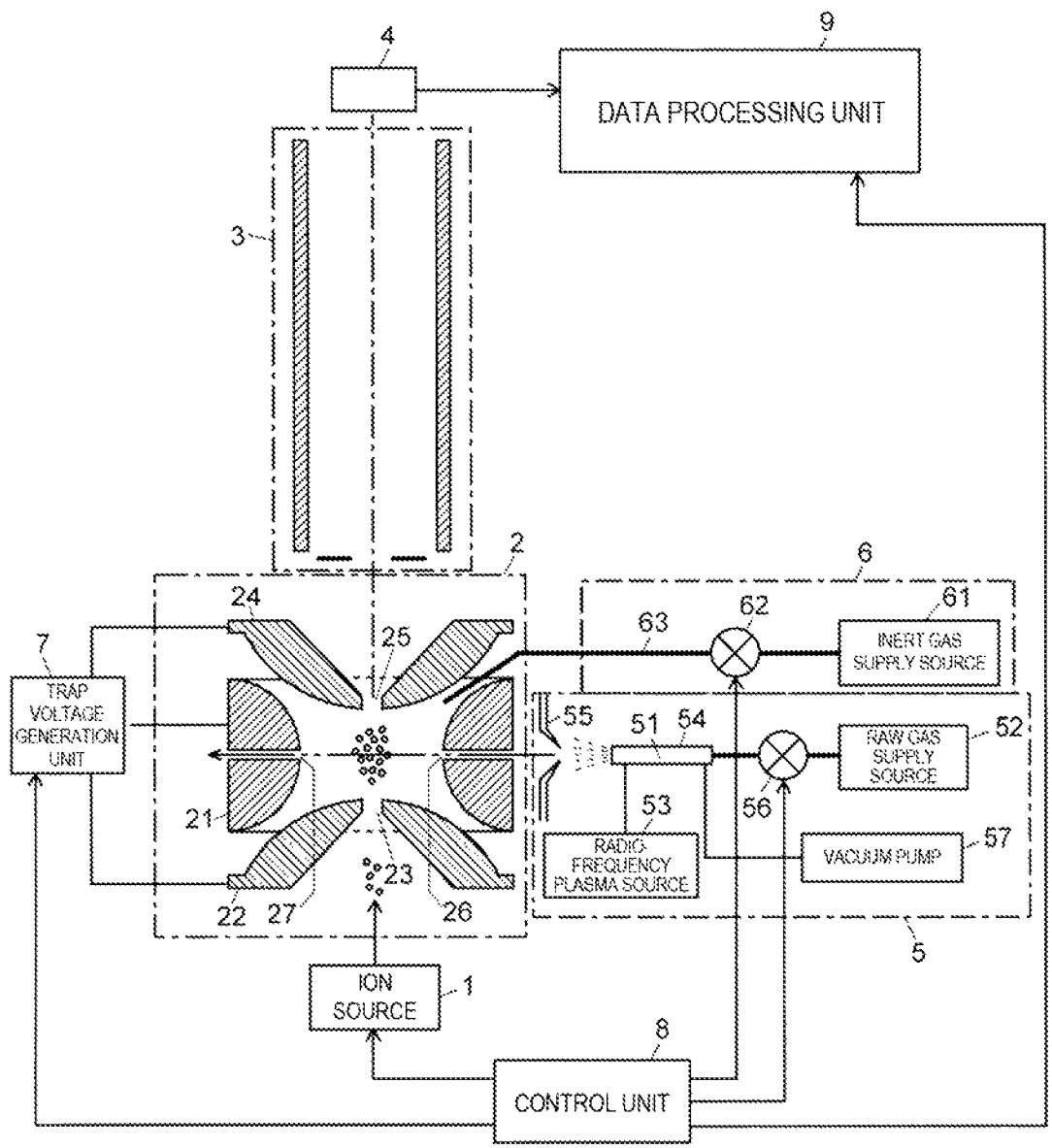
FIG. 1 is a configuration diagram of a main part of an embodiment of a mass spectrometer according to the present invention.

FIG. 1 illustrates a schematic configuration of the ion trap-time-of-flight mass spectrometer (hereinafter, also simply referred to as "mass spectrometer") of the embodiment. The mass spectrometer of the present embodiment includes, inside a vacuum chamber (not illustrated) maintained in a vacuum atmosphere, an ion source 1 which ionizes components in a sample, an ion trap 2 which captures ions generated by the ion source 1 by operation of a radio-frequency electric field, a time-of-flight mass separation unit 3 which separates ions ejected from the ion trap 2 according to a mass-to-charge ratio, and an ion detector 4 which detects separated ions. The ion trap mass spectrometer of the present embodiment further includes a radical irradiation unit 5 for irradiating precursor ions captured in the ion trap 2 with radicals in order to dissociate the ions captured in the ion trap 2, an inert gas supply unit 6 which supplies a predetermined inert gas into the ion trap 2, a trap voltage generation unit 7, a control unit 8, and a data processing unit 9.

The ion source 1 of the mass spectrometer of the present embodiment is a MALDI ion source. In the MALDI ion source, a material (matrix material) that easily absorbs laser light and easily ionizes is applied to the surface of the sample. Thereafter, the matrix material incorporating the sample molecules are microcrystallized, and the sample molecules are ionized by application of laser light on the matrix material. The ion trap 2 is a three-dimensional ion trap including an annular ring electrode 21 and a pair of end cap electrodes (an inlet-side end cap electrode 22 and an outlet-side end cap electrode 24) disposed to oppose each other with the ring electrode 21 between them. A radical particle introduction port 26 and a radical particle releasing port 27 are formed in the ring electrode 21, an ion introduction hole 23 is formed in the inlet-side end cap electrode 22, and an ion ejection hole 25 is formed in the outlet-side end cap electrode 24. In response to an instruction from the control unit 8, the trap voltage generation unit 7 applies one of a radio-frequency voltage and a direct-current voltage or a combined voltage of these voltages to each of the ring electrode 21, the inlet-side end cap electrode 22, and the outlet-side end cap electrode 24 at a predetermined timing.

The radical irradiation unit 5 includes a nozzle 54 having a radical generation chamber 51 formed inside the nozzle 54, a raw gas supply unit (raw gas supply source) 52 for introducing raw gas into the radical generation chamber 51, a vacuum pump (evacuating unit) 57 for evacuating the radical generation chamber 51, an inductively coupled radio-frequency plasma source 53 for supplying a microwave for generating a vacuum electrical discharge in the radical generation chamber 51, a skimmer 55 which has an opening on a central axis of the jet flow from the nozzle 54 and separates diffused raw gas molecules and the like to extract a radical flow having a small diameter, and a valve 56 provided on the flow path from the raw gas supply source 52 to the radical generation chamber 51. As the raw gas, for example, hydrogen gas, oxygen gas, water vapor (water), air or the like can be used. When hydrogen gas is used as the raw gas, hydrogen radicals are generated, and when oxygen gas is used, oxygen radicals are generated. In addition, when water vapor is used as the raw gas, hydroxyl radicals, oxygen radicals, and hydrogen radicals are generated, and when air is used, mainly oxygen radicals and nitrogen radicals are generated.

Figure 2:
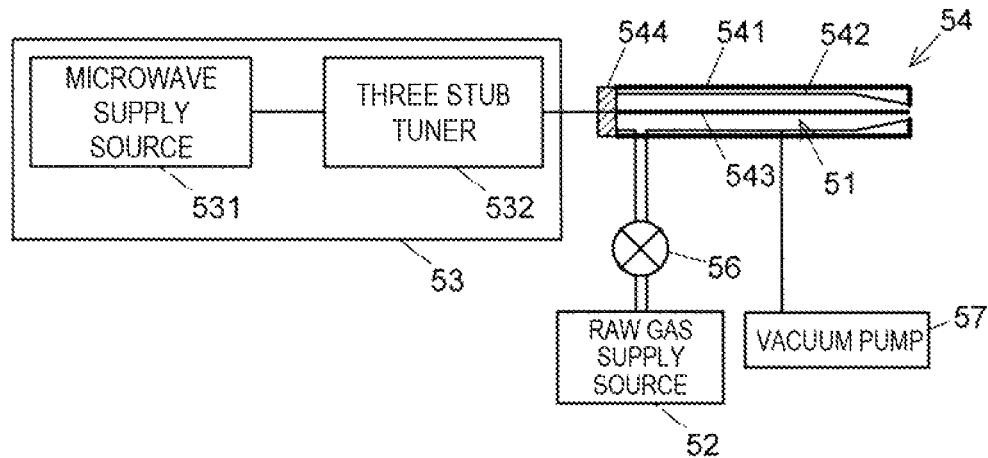
FIG. 2 is a schematic configuration diagram of a radical irradiation unit of the mass spectrometer of the present embodiment.

For the radical irradiation unit 5, for example, one described in Non Patent Literature 3 can be used. A schematic configuration of the radical irradiation unit 5 is illustrated in FIG. 2. Main components of the radical irradiation unit 5 are the raw gas supply source 52, the radio-frequency plasma source 53, the nozzle 54, and the vacuum pump 57. The radio-frequency plasma source 53 includes a microwave supply source 531 and a three stub tuner 532. The nozzle 54 includes a ground electrode 541 constituting an outer peripheral portion and a torch 542 made of Pyrex (registered trademark) glass located inside the ground electrode 541, and the inside of the torch 542 serves as the radical generation chamber 51. Inside the radical generation chamber 51, a needle electrode 543 connected to the radio-frequency plasma source 53 via a connector 544 penetrates in the longitudinal direction of the radical generation chamber 51. A flow path for supplying the raw gas from the raw gas supply source 52 to the radical generation chamber 51 is provided, and a valve 56 for adjusting the flow rate of the raw gas is provided on the flow path.

The inert gas supply unit 6 includes a gas supply source 61 storing helium, argon or the like used as buffer gas or cooling gas and a gas introduction tube 63. The gas introduction tube 63 is provided with a valve 62 for adjusting the flow rate of the gas supplied from the gas supply source 61 to the ion trap 2.

Next, the analysis in the mass spectrometer of the present embodiment will be described. Before starting the analysis, the inside of the vacuum chamber accommodating the ion trap 2 and the like is evacuated to a predetermined degree of vacuum by a vacuum pump (not illustrated). In addition, the inside of the radical generation chamber 51 is evacuated to a predetermined degree of vacuum by the vacuum pump 57. Then, the raw gas is supplied from the raw gas supply source 52 to the radical generation chamber 51 of the radical irradiation unit 5 and the microwave is supplied from the radio-frequency plasma source 53, and thereby radicals are generated in the radical generation chamber 51. As described later, in the present embodiment, hydrogen gas, oxygen gas, water vapor, or the like is used as the raw gas to generate hydrogen radicals, or oxygen radicals and/or hydroxy radicals.

Various ions generated from the sample in the ion source 1 (mainly monovalent ions) are ejected from the ion source 1 in the form of a packet, and the ions pass through the ion introduction holes 23 formed in the inlet-side end cap electrode 22 and introduced inside of the ion trap 2. The ions introduced into the ion trap 2 are captured by a radio-frequency electric field formed in the ion trap 2 by a voltage applied from the trap voltage generation unit 7 to the ring electrode 21. Then, a predetermined voltage is applied from the trap voltage generation unit 7 to the ring electrode 21 and the like, whereby ions having a mass-to-charge ratio other than targeted ions having a specific mass-to-charge ratio are excited and discharged from the ion trap 2. In this way, only precursor ions having a specific mass-to-charge ratio are trapped in the ion trap 2.

Subsequently, the valve 62 of the inert gas supply unit 6 is opened, and an inert gas such as helium gas is introduced into the ion trap 2 to cool the precursor ions. Thus, the precursor ions are converged near a center of the ion trap 2. Then, the valve 56 of the radical irradiation unit 5 is opened, and the gas containing the radicals generated in the radical generation chamber 51 is jetted from the nozzle 54. Then, the gas containing radicals is formed in a beam shape having a small diameter by the skimmer 55 to be jetted into the ion trap 2 from the radical particle introduction port 26 bored in the ring electrode 21, and the precursor ions captured in the ion trap 2 are irradiated with the gas.

At this time, the opening degree and the opening time of the valve 56 (that is, the radical irradiation time of the precursor ions) are adjusted so that the amount of radicals irradiated to the precursor ions becomes a predetermined amount or more. These may be determined in advance based on the results of preliminary experiments and the like.

When the precursor ions in the ion trap 2 are irradiated with the radicals, dissociation induced by unpaired electrons occurs in the precursor ions to generate product ions derived from a peptide. Various product ions generated are captured in the ion trap 2 and cooled by helium gas or the like from the inert gas supply unit 6. Then, a high DC voltage is applied from the trap voltage generation unit 7 to the inlet-side end cap electrode 22 and the outlet-side end cap electrode 24 at a predetermined timing, whereby the ions captured in the ion trap 2 receive acceleration energy and are ejected through the ion ejection holes 25 at once. As mentioned above, the product ions produced here can include both fragment ions and adduct ions.

In this manner, the ions having a constant acceleration energy are introduced into a flight space of the time-of-flight mass separation unit 3, and are separated according to mass-to-charge ratio while flying in the flight space. The ion detector 4 sequentially detects separated ions, and the data processing unit 9 having received a detection signal of the ion detector 4 creates a time-of-flight spectrum in which a time point of ejection of the ions from the ion trap 2 is a time zero, for example. Then, the time-of-flight is converted into a mass-to-charge ratio using mass calibration information which is previously obtained, whereby a product ion spectrum is created. As described below, the data processing unit 9 searches for a mass peak of a predetermined type of product ion to specify a product ion derived from isoaspartic acid, thereby discriminating isoaspartic acid and aspartic acid. That is, the data processing unit 9 of the present embodiment has a function as a product ion specifying unit of the mass spectrometer according to the present invention.

In the mass spectrometer of the present embodiment, isoaspartic acid and aspartic acid are discriminated by dissociating precursor ions by the HAD method or the OAD method. Hereinafter, the details of the above will be described.

Figure 3:
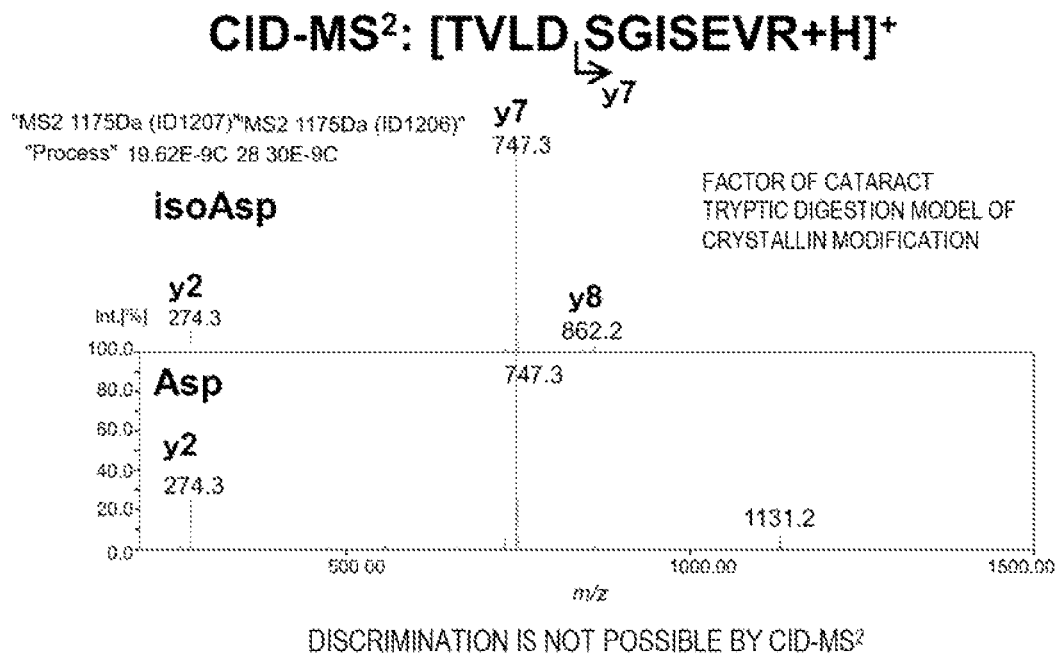
FIG. 3 is a mass spectrum of product ions generated by dissociating isoaspartic acid and aspartic acid by a CID method.

First, a spectrum of product ions generated by dissociating a peptide containing an isoaspartic acid residue and a peptide containing an aspartic acid residue by a collision-induced dissociation (CID) method which has been widely used in the related art will be described. As an example, FIG. 3 illustrates a mass spectrum (product ion spectrum) of product ions generated by dissociating precursor ions derived from a peptide obtained by digesting crystallin (containing an aspartic acid residue) and a crystallin-modified product (containing an isoaspartic acid residue obtained by isomerizing aspartic acid), which are proteins constituting the lens of the eye, with trypsin so as to be fragmented, by the CID method. The upper part illustrates a mass spectrum of a product ion derived from a peptide containing an isoaspartic acid residue, and the lower part illustrates a mass spectrum of a product ion derived from a peptide containing an aspartic acid residue.

As can be seen by comparing the mass spectra of the upper and lower parts in FIG. 3, both mass peaks appear at the same position. That is, when the peptide containing an aspartic acid residue and the peptide containing an isoaspartic acid residue are dissociated by the CID method, there is no difference in product ions to be generated, and the peptide containing an aspartic acid residue and the peptide containing an isoaspartic acid residue, which is an isomer of the aspartic acid residue, cannot be discriminated by dissociation of precursor ions by the CID method.

Figure 4:
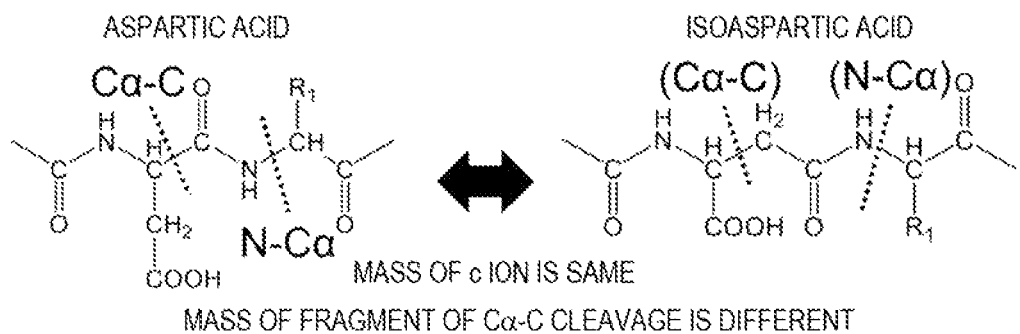
FIG. 4 is a diagram for explaining molecular structures and dissociation positions of aspartic acid and isoaspartic acid.

As illustrated in FIG. 4, even when the aspartic acid residue and the isoaspartic acid residue are dissociated at the position of a N—Cα bond, product ions having different masses are not generated. On the other hand, when both are dissociated at the position of a Cα-C bond, product ions having different masses can be generated. Since the bonds of the peptide main chain are different between the isoaspartic acid residue and the aspartic acid residue, positions corresponding to these bonds in the aspartic acid residue are bracketed in FIG. 4.

Figure 5:
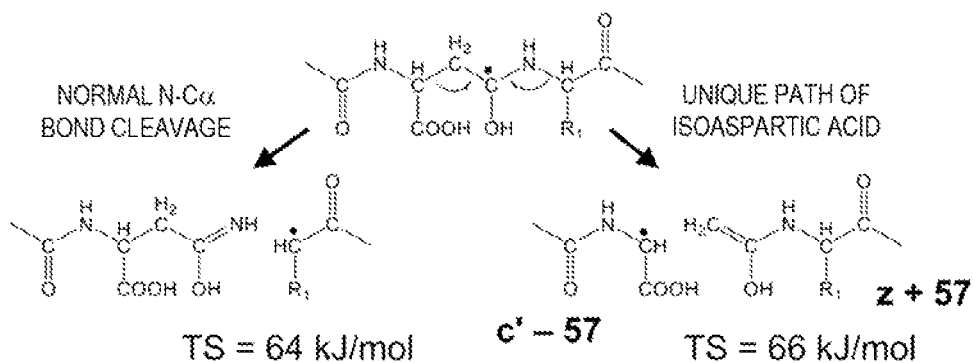
FIG. 5 is a diagram for explaining a quantum chemical calculation result regarding dissociation of isoaspartic acid.

FIG. 5 illustrates the results of quantum chemical calculation performed by the present inventors for the dissociation of the isoaspartic acid residue by the HAD method. When the isoaspartic acid residue is irradiated with a hydrogen radical, the hydrogen radical is attached to the carbon atom of the carboxyl group contained in an amide bond, and then the precursor ions are dissociated in two modes. The first mode is a mode in which dissociation occurs at the position of the N—Cα bond as in the CID method (a mode described as "normal N—Cα bond cleavage" in FIG. 5), and the second mode is a mode in which dissociation occurs at the position of the Cα-C bond (a mode described as "route specific to isoaspartic acid" in FIG. 5). The activation energies from attachment to dissociation of hydrogen radicals are 64 kJ/mol and 66 kJ/mol, respectively, and there is almost no difference. Therefore, when precursor ions derived from a peptide containing an isoaspartic acid residue are dissociated by the HAD method, the product ions dissociated by the Cα-C bond are generated from about half of the precursor ions. On the other hand, aspartic acid is only dissociated at the position of the N—Cα bond. Therefore, isoaspartic acid and aspartic acid can be discriminated by searching for product ions generated by dissociation at the position of the Cα-C bond.

Figure 6:
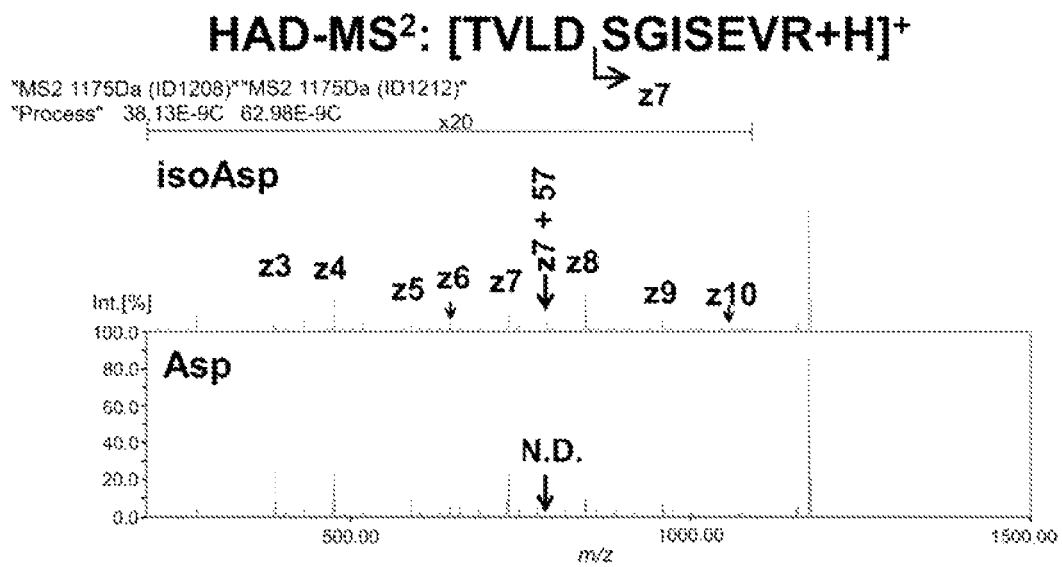
FIG. 6 is a mass spectrum of product ions generated by dissociating a peptide having an isoaspartic acid residue and an aspartic acid residue by a HAD method.
Figure 7:
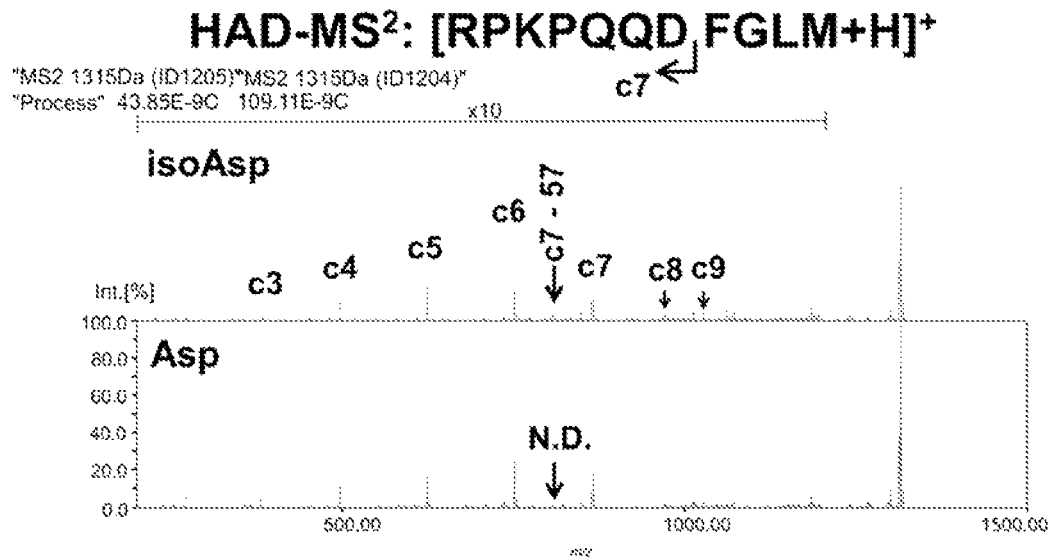
FIG. 7 is a mass spectrum of product ions generated by dissociating another peptide having an isoaspartic acid residue and an aspartic acid residue by the HAD method.

Based on the above calculation results, the results of measuring product ions generated by actually dissociating peptides containing an isoaspartic acid residue and an aspartic acid residue by the HAD method are illustrated in FIG. 6. In the measurement of FIGS. 6 and 7, hydrogen gas was used as a raw gas. The upper part of FIG. 6 illustrates the product ion spectrum of the peptide having an isoaspartic acid residue, and the lower part of FIG. 6 illustrates the product ion spectrum of the peptide having an aspartic acid residue. As illustrated in the upper part of FIG. 6, $z7+57$ ions are detected in the product ion spectrum of the peptide having an isoaspartic acid residue, while $z7+57$ ions are not detected in the product ion spectrum of the peptide having an aspartic acid residue illustrated in the lower part of FIG. 6. Note that $z7$ refers to an ion (z ion) on the C-terminal side generated by dissociation at the position of the N—Cα bond of an aspartic acid residue, and has seven amino acids on the C-terminal side of the binding site. Further, $z7+57$ is an ion having a mass larger by 57 Da than that of the $z7$ ion.

In addition, the results of measuring product ions generated by dissociating peptides containing an isoaspartic acid residue and an aspartic acid residue by the HAD method in the same manner as described above for other peptides are illustrated in FIG. 7. The upper part of FIG. 7 illustrates the product ion spectrum of the peptide having an isoaspartic acid residue, and the lower part of FIG. 7 illustrates the product ion spectrum of the peptide having an aspartic acid residue. As illustrated in the upper part of FIG. 7, $c7-57$ ions are detected in the product ion spectrum of the peptide having an isoaspartic acid residue, while $c7-57$ ions are not detected in the product ion spectrum of the peptide having an aspartic acid residue illustrated in the lower part of FIG. 7. Note that $c7$ refers to an ion (c ion) on the N-terminal side generated by dissociation at the position of the N—Cα bond of an aspartic acid residue, and has seven amino acids on the N-terminal side of the binding site. Further, $c7-57$ is an ion having a mass smaller by 57 Da than that of the $c7$ ion.

From the results illustrated in FIGS. 6 and 7, it is found that isoaspartic acid and aspartic acid can be discriminated by searching for the $z+57$ ion or the $c-57$ ion. Although $z7+57$ ions are detected in FIG. 6 and $c-57$ ions are detected in FIG. 7, which of z ion and c ion is detected depends on the configuration and position of the amino acid contained in the peptide. Specifically, in the peptide illustrated in FIG. 6, since basic arginine (R) to which a hydrogen ion is easily attached is located, a z ion is generated on the C-terminal side of aspartic acid, and in the peptide illustrated in FIG. 7, since basic arginine (R) to which a hydrogen ion is easily attached is located, a c ion is generated on the N-terminal side of aspartic acid.

In addition, as reported by the present inventor in Non Patent Literature 4, when the precursor ions are irradiated with oxygen radicals, the precursor ions derived from a peptide are cleaved at the position of the Cα-C bond of the peptide bond, and a+16 ions are generated. The a+16 ion is an ion in which an oxygen atom is attached to an a ion, which is an ion on the N-terminal side generated by dissociation of a peptide bond at the position of the Cα-C bond, and the mass is increased by 16 Da. In addition, by cleavage at the position of the Cα-C bond of the peptide bond, an x ion can also be generated on the C-terminal side. As described with reference to FIG. 4, when cleavage occurs at the position of the Cα-C bond, product ions (a+16 ions and/or x ions) having different masses are generated from aspartic acid and isoaspartic acid. Therefore, it is considered that isoaspartic acid and aspartic acid can be discriminated from each other also by using water vapor or oxygen gas as a raw gas in place of the hydrogen gas used in the above measurement examples and irradiating the precursor ions with oxygen radicals or hydroxy radicals. In addition, it is also possible to use not only oxygen radicals and hydroxy radicals but also radicals having oxidizing ability similarly to these radicals.

All of the above measurement examples relate to discrimination between isoaspartic acid and aspartic acid contained in a peptide having a known structure, but it is not necessary that the structure of the peptide is known. For example, the structure of the peptide can be estimated by causing the data processing unit 9 to store the names and masses of various materials predicted to be contained in the peptide as a sample component, such as amino acids, and searching for a material in which a difference in mass-to-charge ratio between mass peaks of a product ion spectrum matches the mass of any of the amino acids.

In the above embodiment, the mass spectrometer having the configuration of three-dimensional ion trap-time-of-flight mass separation unit has been described, but a mass spectrometer having another configuration can also be used. For example, it is possible to use a mass spectrometer having a configuration including a front mass separation unit which sorts precursor ions, a collision cell which dissociates the precursor ions by irradiating the precursor ions with radicals, and a rear mass separation unit which separates product ions generated by dissociation of the precursor ions in the collision cell according to a mass-to-charge ratio. An example of such a mass spectrometer is a triple quadrupole mass spectrometer. In this case, radicals may be injected from the nozzle into the collision cell to irradiate precursor ions passing through the collision cell.

Aspects

It is understood by those skilled in the art that the plurality of exemplary embodiments described above are specific examples of the following aspects.

(First Aspect)

A first aspect of the present invention is a method for analyzing isoaspartic acid by dissociating precursor ions derived from a sample component and generating and analyzing product ions, the method including:

generating product ions by irradiating the precursor ions with hydrogen radicals or radicals having oxidizing ability to dissociate the precursor ions;

separating and detecting the product ions according to a mass-to-charge ratio; and specifying product ions derived from isoaspartic acid based on a mass-to-charge ratio of the product ions.

(Fifth Aspect)

A fifth aspect of the present invention is a mass spectrometer for analyzing isoaspartic acid by dissociating precursor ions derived from a sample component and generating and analyzing product ions, the mass spectrometer including:

a reaction chamber into which the precursor ions are introduced;

a radical generation unit configured to generate a hydrogen radical or a radical having oxidizing ability;

a radical irradiation unit configured to irradiate an inside of the reaction chamber with radicals generated by the radical generation unit;

a separation and detection unit configured to separate and detect product ions generated by dissociation of the precursor ions by reaction with the radicals according to a mass-to-charge ratio; and a product ion specifying unit configured to specify product ions derived from isoaspartic acid on a basis of a mass-to-charge ratio of the product ions.

In the method for analyzing isoaspartic acid of the first aspect and the mass spectrometer of the fifth aspect, precursor ions derived from the sample component are irradiated with hydrogen radicals or radicals having oxidizing ability to generate the product ions. The radical having oxidizing ability is, for example, an oxygen radical or a hydroxy radical. The ion dissociation method for irradiating precursor ions with these radicals is a hydrogen-attachment dissociation (HAD) method and an oxygen-attachment dissociation (OAD) method proposed by the present inventor in Patent Literature 1.

The present inventor has found that when the precursor ions derived from isoaspartic acid are dissociated by the HAD method, c+57 ions and z−57 ions which characterize isoaspartic acid (and not generated from aspartic acid) are generated as in the ETD method. In addition, the present inventor has found that when the precursor ions derived from isoaspartic acid are dissociated by the OAD method, in which oxygen radicals or hydroxy radicals are attached to precursor ions to dissociate the precursor ions, an a+16 ion which characterizes isoaspartic acid (not generated from aspartic acid) is generated. The a+16 ion is an ion having a mass larger by 57 than that of the ion (c ion) on the N-terminal side which is generated by cleaving the Cα-C bond of the peptide main chain of aspartic acid.

That is, the present inventor has found that isoaspartic acid can be discriminated from aspartic acid and analyzed by separating and detecting product ions generated by dissociating precursor ions derived from a sample component according to a mass-to-charge ratio and specifying ions corresponding to these detected ions. The HAD method and the OAD method are methods of dissociating precursor ions by radical addition, and can be used regardless of the polarity or valence of ions to be dissociated. Therefore, the precursor ions derived from a sample component can be efficiently dissociated, and the isoaspartic acid and the aspartic acid, which is an isomer of the isoaspartic acid can be easily discriminated and analyzed.

(Second Aspect)

A method for analyzing isoaspartic acid according to a second aspect of the present invention is the method for analyzing isoaspartic acid of the first aspect, in which the product ions derived from the isoaspartic acid are specified by searching for a c+57 ion or a z−57 ion.

(Sixth Aspect)

A mass spectrometer according to a sixth aspect of the present invention is the mass spectrometer according to the fifth aspect, in which the product ion specifying unit is configured to search for a c+57 ion or a z−57 ion.

In the method for analyzing isoaspartic acid of the second aspect and the mass spectrometer of the sixth aspect, it is possible to discriminate isoaspartic acid and aspartic acid by searching for a c+57 ion or a z−57 ion unique to isoaspartic acid, which is generated by the HAD method or the like in which hydrogen radicals are irradiated.

(Third Aspect)

A method for analyzing isoaspartic acid according to a third aspect of the present invention is the method for analyzing isoaspartic acid according to the first aspect or the second aspect, in which the product ions derived from the isoaspartic acid are specified by searching for an a+16 ion.

(Seventh Aspect)

A mass spectrometer according to a seventh aspect of the present invention is the mass spectrometer according to the fifth aspect or the sixth aspect, in which the product ion specifying unit is configured to search for an a+16 ion.

In the method for analyzing isoaspartic acid of the third aspect and the mass spectrometer of the seventh aspect, it is possible to discriminate isoaspartic acid and aspartic acid by searching for an a+16 ion unique to isoaspartic acid, which is generated by the OAD method or the like in which a radical having oxidizing ability is irradiated.

(Fourth Aspect)

A method for analyzing isoaspartic acid according to a fourth aspect of the present invention is the method for analyzing isoaspartic acid according to the third aspect, in which the precursor ions are irradiated with oxygen radicals and/or hydroxy radicals.

(Eighth Aspect)

A mass spectrometer according to an eighth aspect of the present invention is the mass spectrometer of the seventh aspect, in which the radical generation unit is configured to generate an oxygen radical and/or a hydroxy radical.

In the mass spectrometer of the seventh aspect, it is possible to infer the ratio of the component having a cis type unsaturated bond and the component having a trans type unsaturated bond contained in the sample component without bothering the user.

REFERENCE SIGNS LIST

1 . . . Ion Source
2 . . . Ion Trap
21 . . . Ring Electrode
22 . . . Inlet-Side End Cap Electrode
23 . . . Ion Introduction Hole
24 . . . Outlet-Side End Cap Electrode
25 . . . Ion Ejection Hole
26 . . . Radical Particle Introduction Port
27 . . . Radical Particle Releasing Port
3 . . . Time-Of-Flight Mass Separation Unit
4 . . . Ion Detector
5 . . . Radical Irradiation Unit
51 . . . Radical Generation Chamber
52 . . . Raw Gas Supply Source
53 . . . Radio-Frequency Plasma Source
531 . . . Microwave Supply Source
532 . . . Three Stub Tuner
54 . . . Nozzle
541 . . . Ground Electrode
542 . . . Torch
543 . . . Needle Electrode
544 . . . Connector
55 . . . Skimmer
56 . . . Valve
57 . . . Vacuum Pump
6 . . . Inert Gas Supply Unit
61 . . . Gas Supply Source
62 . . . Valve
63 . . . Gas Introduction Pipe
7 . . . Trap Voltage Generation Unit
8 . . . Control Unit
9 . . . Data Processing Unit

The invention claimed is:

1. A method for analyzing isoaspartic acid by dissociating precursor ions derived from a sample component and generating and analyzing product ions, the method comprising:
generating product ions by irradiating the precursor ions with hydrogen radicals or radicals having oxidizing ability to dissociate the precursor ions;
separating and detecting the product ions according to a mass-to-charge ratio; and
specifying product ions derived from isoaspartic acid based on a mass-to-charge ratio of the product ions.

2. The method for analyzing isoaspartic acid according to claim 1, wherein
the precursor ions are irradiated with hydrogen radicals and
the product ions derived from the isoaspartic acid are specified by searching for a c+57 ion or a z−57 ion.

3. The method for analyzing isoaspartic acid according to claim 1, wherein the product ions derived from the isoaspartic acid are specified by searching for an a+16 ion.

4. The method for analyzing isoaspartic acid according to claim 3, wherein the precursor ions are irradiated with oxygen radicals and/or hydroxy radicals.

5. A mass spectrometer for analyzing isoaspartic acid by dissociating precursor ions derived from a sample component and generating and analyzing product ions, the mass spectrometer comprising:
a reaction chamber into which the precursor ions are introduced;
a radical generation unit configured to generate a hydrogen radical or a radical having oxidizing ability;
a radical irradiation unit configured to irradiate an inside of the reaction chamber with radicals generated by the radical generation unit;
a separation and detection unit configured to separate and detect product ions generated by dissociation of the precursor ions by reaction with the radicals according to a mass-to-charge ratio; and
a product ion specifying unit configured to specify product ions derived from isoaspartic acid on a basis of a mass-to-charge ratio of the product ions.

6. The mass spectrometer according to claim 5, wherein
the radical generation unit is configured to generate a hydrogen radical and
the product ion specifying unit is configured to search for a c+57 ion or a z−57 ion.

7. The mass spectrometer according to claim 5, wherein the product ion specifying unit is configured to search for an a+16 ion.

8. The mass spectrometer according to claim 7, wherein the radical generation unit is configured to generate an oxygen radical and/or a hydroxy radical.

* * * * *